United States Patent [19]

Bucalo

[11] 4,013,063

[45] Mar. 22, 1977

[54] IMPLANT FOR REVERSIBLY PREVENTING CONCEPTION

[76] Inventor: Louis Bucalo, 155 Roberts St., Holbrook, N.Y. 11741

[22] Filed: Apr. 14, 1975

[21] Appl. No.: 568,138

Related U.S. Application Data

[63] Continuation-in-part of Ser. No. 513,292, Oct. 9, 1974.

[52] U.S. Cl. .............................. 128/1 R; 128/1.3; 137/827; 210/223; 251/65
[51] Int. Cl.² ........................................ A61B 19/00
[58] Field of Search ............ 128/1 R, 1.3, 1.5, 130, 128/DIG. 25; 251/65; 210/222, 223; 138/43, 46; 137/251 A, 827

[56] References Cited

UNITED STATES PATENTS

| | | | |
|---|---|---|---|
| 3,477,948 | 11/1969 | Inoue | 210/223 |
| 3,731,670 | 5/1973 | Loe | 128/1 R |
| 3,815,578 | 6/1974 | Bucalo | 128/1 R |

*Primary Examiner*—William E. Kamm
*Attorney, Agent, or Firm*—Steinberg and Blake

[57] ABSTRACT

An implant to be situated in a vas deferens for reversibly preventing conception. A pair of open-ended tubular structures respectively have inner end regions adjacent but spaced from each other and fluid-tightly joined with a housing having an interior space through which fluid can flow between the pair of tubular structures. Within the housing are a plurality of fine particles capable of responding to magnetic forces. A permanent magnet is provided for attracting the particles to a conception-preventing position where the particles form a body of sufficient density to retain sperm while of insufficient density to prevent the sperm-carrying fluid from flowing through the body and through the tubular structures.

15 Claims, 2 Drawing Figures

FIG. I

IMPLANT FOR REVERSIBLY PREVENTING CONCEPTION

CROSS REFERENCE TO RELATED APPLICATION

This application is a continuation-in-part of copending application Ser. No. 513,292, filed Oct. 9, 1974 and entitled CONCEPTION-PREVENTION AND VARIABLE FILTERING OR FLOW CONTROL DEVICES AND METHODS.

BACKGROUND OF THE INVENTION

The present invention relates to implants to be situated in the vas deferentia of adult male animals for the purpose of controlling conception.

Implants of this type are generally know. For example, such implants are capable of blocking the flow of fluid through a vas deferens in order to prevent conception, and of course there are known implants which can be placed in a position which will again permit fluid to flow through a vas deferens to that it is possible in this way to achieve reversible contraception, with the capability of conceiving being restored when desired.

However, the problem with implants of the above general type is that they operate, when preventing conception, by completely blocking the flow of fluid through a vas deferens. Such complete blockage of the flow of fluid is highly undesirable. Thus, the preventing of sperm flow is undesirably accompanied by preventing of flow of the fluid which carries the sperm, and thus beneficial effects resulting from the flow of this latter fluid are prevented with conventional implants as referred to above. The fluid which flows through the vas deferens serves not only to carry sperm but also to perform other functions such as supplying certain hormones and enzymes to the body, maintaining the lumen of the vas deferens in an open condition enabling fluid to flow properly therethrough, and avoiding undesirable build-up of pressure. Moreover, with complete blockage of flow through the vas deferens there is a tendency for the latter to close upon itself downstream of the implant, so that when flow is restored with conventional implants here is still difficulty in achieving reliable flow of fluid through the vas deferens, particularly if the latter has been completely closed over a long period of time.

SUMMARY OF THE INVENTION

It is accordingly a primary object of the present invention to provide an implant which will avoid the above drawbacks. In particular, it is an object of the present invention to provide an implant which will permit the fluid which carries the sperm to flow through the vas deferens while at the same time retaining, when it is desired to prevent conception, sperm so as to prevent them from being carried along with the fluid, with the exent to which sperm are retained in this way being sufficiently great to prevent conception in a highly reliable manner.

It is furthermore an object of the present invention to provide an implant which can readily be placed in a condition where fluid with sperm therein can flow freely through the vas deferens so that the capability of conceiving can be restored very easily and conveniently whenever desired.

It is furthermore an object of the present invention to provide an implant of the above general type which can be introduced into the vas deferens without creating undesirable kinks or the like therein which might undesirably prevent normal fluid flow through the vas deferens.

Also, it is an object of the present invention to provide an implant of the above general type which is composed of simple rugged elements which can be conveniently manipulated and which can be situated in the body without creating any particular discomfort and while being fully compatible with the body of the individual who receives the implant of the invention.

According to the invention the implant includes a pair of coaxial tubular means which respectively have inner end regions situated adjacent but spaced from each other along the common axis of the tubular means, while the latter also have outer ends distant from and directed away from each other. An intermediate housing is fluid-tightly connected with the pair of tubular means at the inner end regions thereof so that the pair of tubular means can communicate with each other through the space within the intermediate housing. The intermediate housing has in its interior a plurality of fine particles which can assume a conception-preventing position situated in the path of fluid flow between the pair of tubular means as well as a conception-enabling position situated beyond the path of fluid flow between the pair of tubular means. These particles are capable of responding to magnetic forces, and a permanent magnet surrounds one of the tubular means at its inner end region while being situated at the exterior of the housing for the purpose of attracting he particles to their conception-preventing position where the particles are urged toward each other sufficiently to form a body the density of which is great enough to prevent sperm from flowing through this body while at the same time the body is sufficiently porous to permit the fluid which carries the sperm to flow through the body, so that in this way fluid which normally carries sperm can flow through the vas deferens while sperm are retained by the particles which are in their conceptionpreventing position. The pair of tubular means respectively carry at their inner end regions a porous means through which the particles cannot flow but through which the fluid can flow, so that in this way the particles are retained within the intermediate housing. When conception is desired the particles are readily situated beyond the path of flow of fluid between the pair of tubular means. For example if the particles are of a magnetically soft material capable of responding to magnetic forces without becoming permanently magnetized, then it is only necessary to situate adjacent the implant of the invention a magnet stronger than the above permanent magnet for attracting the particles away from their conception-preventing position to their conception-enabling position. Such a magnet which is stronger than the permanent magnet of the implant of the invention can readily be situated at the exterior of the body of the individual provided with the implant, in the region of the scrotum, for example, for the purpose of attracting the particles to their conception-enabling position. However, it is also possible to provide a second permanent magnet into the field of which the particles are transferred away from their conception-preventing location, so that when in the field of this second magnet they will be retained thereby in their conception-enabling position. Furthermore it is possible simply to demagnetize the magnet as well as the particles if they retain any residual magnetism and permit the latter simply to fall by gravity to their conception-enabling position.

BRIEF DESCRIPTION OF DRAWINGS

The invention is illustrated by way of example in the accompanying drawings which form part of this application and in which.

DESCRIPTION OF PREFERRED EMBODIMENTS

Figure 1:
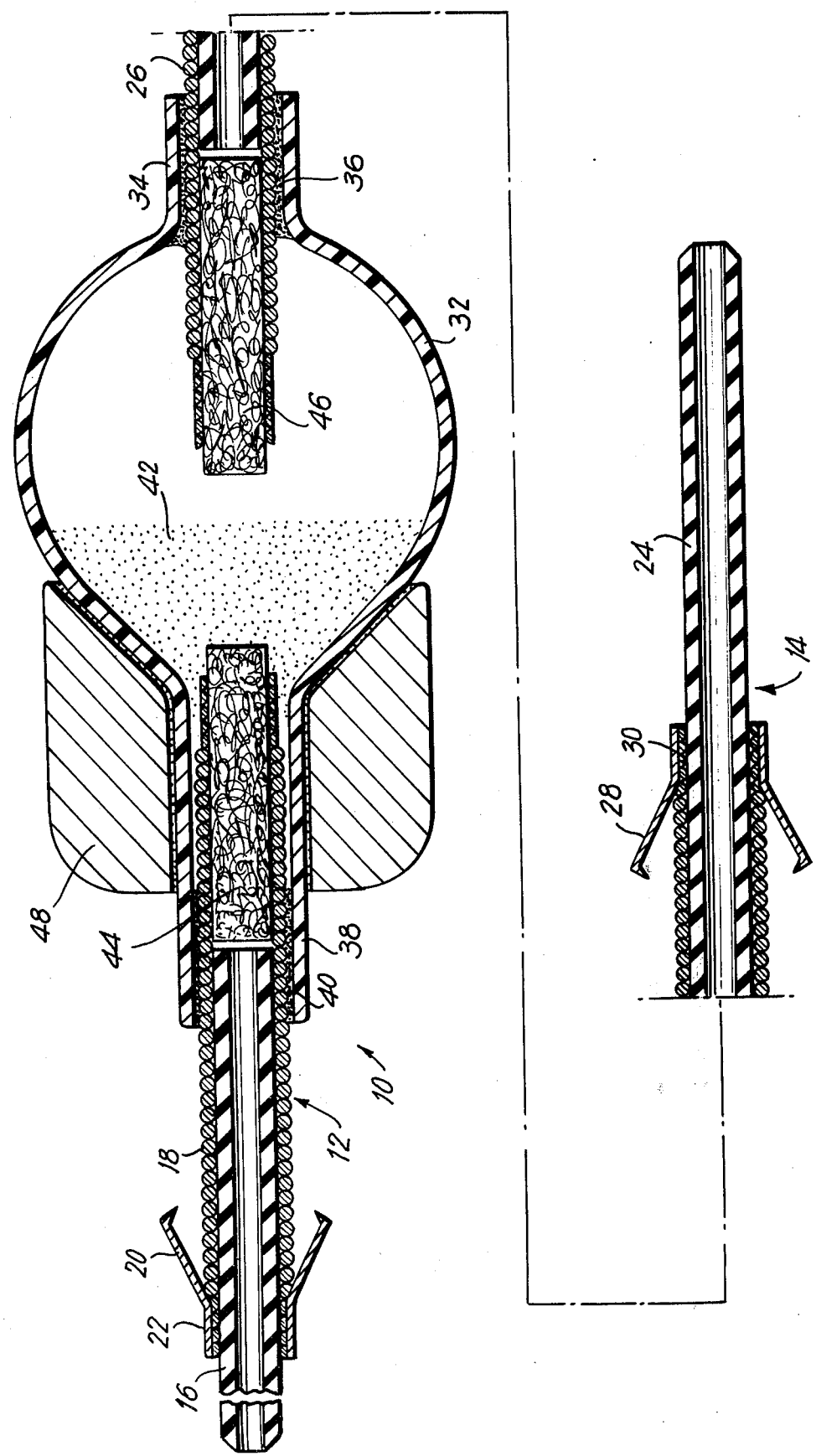
FIG. 1 is a longitudinal sectional elevation of an implant of the invention, taken in a plane containing the common axis of the pair of tubular means thereof, with the implant being shown in FIG. 1 enlarged many times since the distance between the outer tips of the pair of tubular means in the actual implant is on the order of 1 inch.

Referring now to FIG. 1 of the drawings, the implant 10 which is illustrated therein includes a pair of tubular means 12 and 14. The pair of tubular means 12 and 14 are coaxial, with the tubular means 14 being situated upstream of the tubular means 12 in that the fluid in the vas deferens first enters the tubular means 14 and flows along the interior thereof toward the tubular means 12.

The tubular means 12 has an inner tubular member 16 which carries at its exterior a tissue-ingrowth means 18 which may be made of any filamentary material such as gold wire which is wound around and fixed to the exterior surface of the inner tubular member 16. The inner tubular member 16 is flexible and extends outwardly beyond the tissue-ingrowth means 18. This inner tubular member 16 may be made, for example, of a suitable silicone rubber which is compatible with the body, such as a Silastic type of material, or the inner tubular member 16 may be made of a metal such as a suitable stainless steel wire which is coiled and which has its convolutions engaging each other to form in this way the equivalent of a flexible metal tube.

The tissue-ingrowth means 18 may be made of gold wire and is shown in an idealized condition in the drawing. This tissue-ingrowth means 18 is made of a fine gold wire which is wound in several layers around the exterior of the tubular member 16, and it will be noted that the tissue-ingrowth means 18 extends inwardly beyond the tubular member 16 through a substantial distance toward the tubular means 14. At its outer end region, beyond which the inner tubular member 16 extends, the tissue-ingrowth means 18 fixedly carries a plurality of flexible barbs 20. There may be three such barbs angularly spaced one from the next by 120° about the axis of the tubular member 16. These barbs project from and may be integral with a ring 22 which is fixed to the ingrowth means 18 as by being swaged onto the latter.

The tubular means 14 is of the same general construction as the tubular means 12. Thus the tubular means 14 also has an inner flexible tubular member which may be in the form of a tube consisting of coils of stainless steel or which may be made of silicone rubber material such as a Silastic type of material. This inner tubular member 24 fixedly carries at its exterior the tissue ingrowth means 26 which may be identical with the tissue ingrowth means 18 and which also extends inwardly beyond the inner end of the tubular member 24 toward the tubular means 12. Also in the same way as the tubular means 12 the tubular means 14 is provided with barbs 28 which are integral with and project from a ring 30 swaged onto the tissue-ingrowth means 26 at the outer end region of the latter beyond which the tubular member 24 extends as illustrated.

An intermediate housing means formed by a housing 32 is fluid-tightly connected with the pair of tubular means 12 and 14 at their inner end regions so that the tubular means 12 and 14 are capable of communicating with each other through the space within the housing 32. The housing 32 is made of a non-magnetic material such as a suitable plastic and it may be transparent so that it is possible to look through the housing into the interior thereof, although transparency of the housing 32 is not essential. It will be noted that the intermediate portion of the housing 32 is of a substantially spherical configuration and has a diameter substantially greater than the diameter of either one of the tubular means 12 and 14 so that the cross-sectional area of the housing 32 is substantially greater than the cross-sectional area of each of the tubular means 12 and 14. The housing 32 has a tubular extension 34 which receives the tissue ingrowth means 26 and is fluid-tightly connected with the tubular means 14 by way of a suitable adhesive 36 such as a silicone rubber medical adhesive, a Silastic type of adhesive being suitable for this purpose. It will be noted that the tubular member 24 extends partly into the extension 34 while the tissue ingrowth means 26 extends beyond the tubular member 24 through and beyond the extension 34 and through a substantial distance into the interior of the housing 32. Thus in the illustrated example the tissue-ingrowth means 26 extends to the region of the center of the housing 32.

The tubular means 12 is received at its inner end region within a tubular extension 38 of the housing 32, this extension 38 being longer than the extension 34, as illustrated. Also in this case the tubular means 12 is fluid-tightly connected with the housing 32 by way of a suitable adhesive 40 which may be the same as the adhesive 36. In this case the tissue ingrowth means 18 extends inwardly beyond the inner end of the tubular member 16 but only up to the region where the extension 38 projects from the spherical part of the housing 32.

Within the housing 32 is situated a particulate means made up of a plurality of particles 42. For a purpose referred to below the particles 42 are made of a material which will respond to magnetism. In order to retain the extremely fine particles 42, which appear to the naked eye as a powder, reliably within the interior of the housing 32, each tubular means carries at its inner end region a porous means through which fluid can flow but having interior spaces which are too small to receive the particles 42. Thus it will be seen that the tissue ingrowth means 18 is wound around a cylindrical block 44 which forms the porous means carried by the tubular means 12, while the tissue-ingrowth means 26 is wound around a similar block 46 which forms the porous means carried by the tubular means 14. Each of the blocks 44 and 46 is preferably made of fine gold filament which is gathered together and compressed so as to be given the illustrated configuration with the compression used in deforming and gathering together the filamentary gold wire being sufficiently great to define between the filamentary material small interstices which provide for each of the means 44 and 46 the degree of porosity according to which fluid can flow through each of the means 44 and 46 while the particles 42 cannot be carried through the means 44 and 46. Thus, it will be seen from the drawing that the tissue ingrowth means 18 and 26 serve to connect the porous means 44 and 46, respectively, to the tubular means 12 and 14 by being wound tightly around the porous means 44 and 46. Moreover the inner end regions of the tissue ingrowth means 18 and 26 are swaged so as to be pressed inwardly against the blocks 44 and 46 in order to fix the latter in the positions indicated in the drawing where it will be noted that the blocks 44 and 46 are spaced slightly beyond the inner ends of the tubular members 16 and 24. Furthermore it will be noted that the porous means 44 and 46 respectively extend through a slight distance inwardly beyond the inner ends of the tissue ingrowth means 18 and 26. Thus the pair of tissue ingrowth means 18 and 26 serve not only the purpose of promoting ingrowth of tissue into intimate contact with the exterior tubular means 12 and 14 beyond the extensions 34 and 38 of the housing 32, but in addition the pair of tissue ingrowth means 18 and 26 serve to connect the pair of porous means 44 and 46 to the pair of tubular means 12 and 14, respectively.

The above-described means formed by a permanent magnet implant of the invention is completed by a permanent magnet 48 which surrounds the inner end region of the tubular means 12. In the illustrated construction the permanent magnet 48 is fixed directly to the exterior surface of the housing 32 by a suitable adhesive which may also be a silicone rubber medical adhesive. It will be noted that the permanent magnet 48 is formed with an axial bore which receives the tubular extension 38 while this bore is enlarged at one end so as to conform to the configuration of the exterior surface of the housing 32 as illustrated.

It is to be noted that the structure of the invention is of a circular configuration in any plane perpendicular to the common axis of the pair of tubular means 12 and 14. Moreover, the dimensions of the spherical housing 32 are such that not only is the interior of the housing of a greater cross sectional area than the interior of either of the tubular means 12 and 14 but in addition the housing extends radially outwardly beyond the permanent magnet 48.

The permanent magnet 48 may be made of an alloy of platinum and cobalt so that it forms a strong permanent magnet which at the same time is compatible with the body of the individual receiving the implant. The fine particles 42 are preferably made of a magnetically soft material such as soft-iron of the type used in solenoids or nickel. In either case, which is to say either when the particles are made of nickel or when they are made of a soft iron they are gold-plated so as to be compatible with the body. Such particles are capable of responding to magnetic forces without being capable of themselves becoming permanent magnets. However, it is also possible to use for the structure of the invention particles made of a material which is capable of becoming a permanent magnet such as Alnico, an alloy of aluminum, nickel, and cobalt, which is known to have strong magnetic properties.

With the construction described above and shown in the drawing, the permanent magnet 48 will attract the particles 42 into the conception-preventing position indicated in the drawing. The quantity of particles 42 is sufficiently great to enable them to form, under the influence of the magnet 48, a body of sufficient density to retain sperm which thus cannot flow through the body formed by the particles 42 into the downstream tubular means 12. However, the fluid which normally carries the sperm can flow through the body formed by the magnetically-attracted particles 42 and through the porous means 44 into the tubular member 16.

The above-described implant can be introduced into a vas deferens according to known surgical procedures. Thus, surgical access is provided in a known way to a vas deferens part of which may be excised so that the resulting tubular free ends of the vas deferens can receive the tubular means 12 and 14 with the vas deferens being drawn at its free ends resulting from the above excision all the way up to the extremities of the extensions 34 and 38 of the housing 32. The barbs 20 and 28 will dig into the tissue which defines the lumen of the vas deferens so as to prevent withdrawal thereof from the implant while maintaining the vas deferens immobilized between the barbs and the extremities of the housing 32. Thus the parts of the vas deferens which engage the tissue ingrowth means where the latter projects beyond the housing 32 will rapidly grow into the tissue ingrowth means into intimate contact with the exterior of the tubular members 16 and 24 providing an exceedingly secure connection in an extremely effective manner and in a minimum time. The flexibility of the tubular members 16 and 24 where they project beyond the tissue ingrowth means prevents kinking of the vas deferens so that a smooth flow through the latter is assured.

As was pointed out above, the total length of the implant of the invention from the outer end of the tubular member 16 to the outer end of the tubular member 24 is on the order of 1 inch. The spherical housing 32 can have an inside diameter on the order of 0.165 inch while the thickness of the wall of the housing 32 is on the order of 0.005 inch. As was pointed out above the housing 32 is made of a non-magnetic material such as a suitable plastic which may be, for example, polyethylene. In addition, the housing 32 may be made of gold, or it may be made of a suitable non-magnetic metal such as, for example, stainless steel. The barbs 20 and 28 may be made of stainless steel. The tubular member 24 may extend outwardly beyond the tissue ingrowth means 26 through a distance of, for example, 0.190 inch, while the tissue ingrowth means 26 may extend outwardly beyond the extension 34 through a distance of, for example, 0.130 inch. The extension 34 itself may have a length on the order of 0.060 inch, and the extension 38 may project through the same distance outwardly beyond the permanent magnet 48 which may have an outside diameter on the order of 0.156 inch, and an inside diameter on the order of 0.050 inch, and a length on the order of 0.125 inch. Thus, the distance from the outer end of tissue ingrowth means 18 to the outer end of tissue ingrowth means 26 may be on the order of 0.620 inch, while the distance between the outer extremities of the extensions 34 and 38 may be on the order of 0.360 inch and the distance from the inner end of porous barrier 46 to the outer end of tissue ingrowth means 26 may be on the order of 0.282 inch. Each barrier 44 and 46 can project inwardly beyond the tissue ingrowth means surrounding the same through a distance on the order of 0.010 inch. Each of the porous means 44 and 46 may have an outside diameter on the order of 0.025 inch and may have a length on the order of 0.135 inch.

Thus, with an implant as described above situated in a vas deferens, the fluid which carries the sperm can flow into the tubular means 14 and through the porous barrier 46 into the interior of the housing 32. From the latter the fluid can flow through the body formed by the magnetically attracted particles 42 while the sperm will be retained by the latter, and then the fluid without sperm therein in sufficient numbers to provide conception can continue to flow through the porous means 44 and the tubular means 16.

When it is desired to provide for the particles 42 a conception-enabling position, it is only necessary to situate next to the skin of the individual who has implants of the above type introduced into his vas deferentia a suitable permanent magnet, situated in the region of the scrotum, for example, this latter exterior permanent magnet being stronger than the permanent magnet 48 to an extent sufficient to attact the particles 42 away from their conception-preventing position shown in the drawing to a conception-enabling position where the particles 42 are situated to one side of the common axis of the tubular means 12 and 14 beyond the path of flow of fluid between the pair of tubular means 12 and 14. Of course the porosity of the barriers 44 and 46 is sufficiently great to permit sperm to freely flow therethrough, this porosity only being small enough to prevent the particles 42 from flowing through the barriers 44 and 46. Thus sperm will now be able to flow through the implant of the invention so that the conception-preventing implant of the invention is easily and conviently placed in a condition where the capability of conceiving is again established. A stronger permanent magnet which is stronger thant the magnet 48 can be held by a suitable strap, for example, at a suitable location for attracting the particles 42 into their conception-enabling position, in the case where the particles are made of a material such as soft iron which responds to magnetic forces but which cannot become permanently magnetized.

However, as was pointed out above, these particles 42 may be made of a material which can become permanently magnetized. In this case, by situating a suitable alternating field at the exterior of the individual provided with the implants of the invention adjacent to these implants, it is possible to demagnetize the permanent magnet 48 as well as the particles 42 so that they will simply fall into the interior of the housing 32 into the space surrounding the tissue-ingrowth means 26 where it extends into the interior of the housing 32, and the thus-demagnetized particles will simply remain in this space out of the path of flow between the pair of tubular means 12 and 14 so that the capability of again conceiving is readily reestablished with such a construction also.

Figure 2:
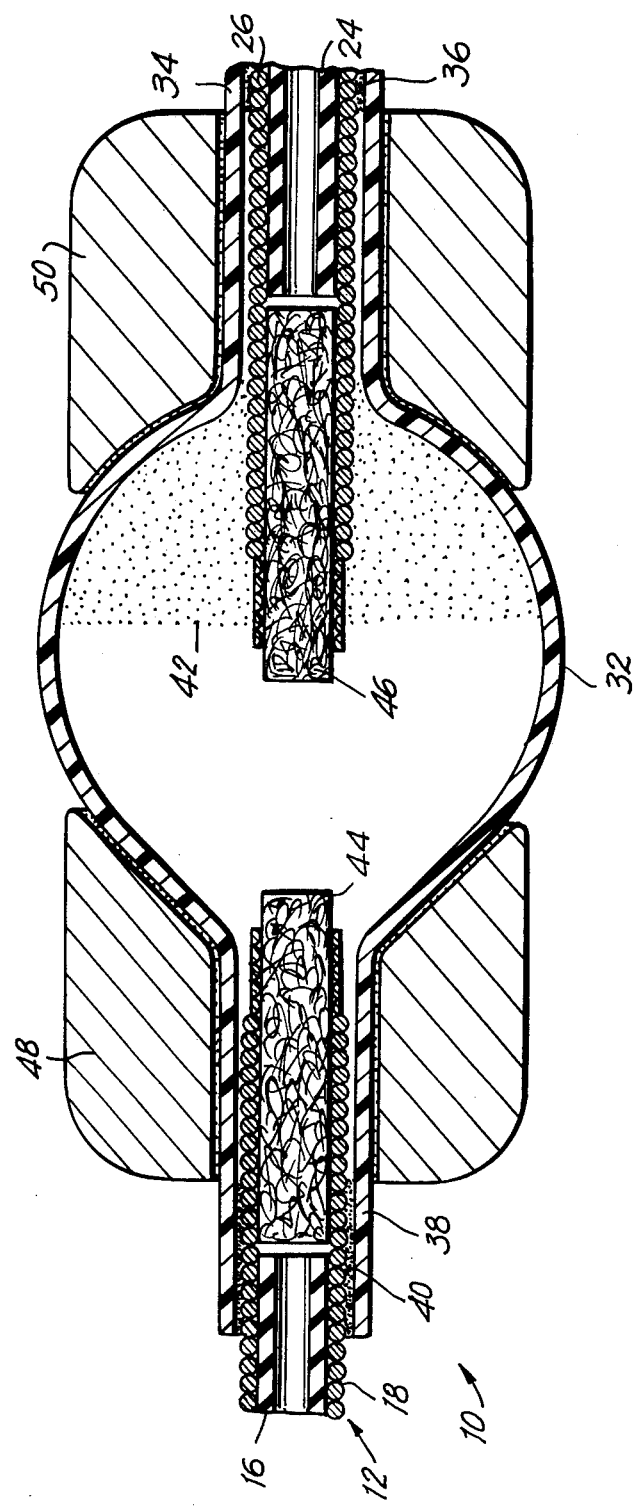
FIG. 2 is a fragmentary sectional elevation showing a central part of an implant of a construction slightly different from that of FIG. 1.

A further possibility in this latter connection is illustrated in FIG. 2. Thus it will be seen that in addition to the magnet 48 at one side of the housing, the housing carries a second magnet 50 at the opposite side thereof, this magnet 50 being similar to the magnet 48 but being oppositely oriented as illustrated. Thus, with this construction it is also possible simply by applying at the exterior of the body of the individual provided with the implant a magnet stronger than the magnet 48 to attract the particles 42 away from the magnet 48 and into the field of the magnet 50 which will under these circumstances attract all of the particles 48 into the space within the housing which surrounds the inner end region of the tubular means 14. It will be seen that the particles are shown in this latter position in FIG. 2. Thus with this construction when it is desired to provide the conception-enabling condition, it is only necessary with an exterior magnet to displace the particles from the field of the magnet 48 into the field of the magnet 50 to be retained by the latter in a position where the particles will not block the flow of sperm. Thus with this construction it is not necessary to retain at the exterior of the body an additional magnet stronger than the magnet 48. However, it is also possible to demagnetize the magnet 48 so that the particles will then become attracted to the second magnet 50, so that through this procedure it is not necessary to utilize an exterior magnet. Then when the particles are to be returned to their conception-preventing condition, the magnet 50 can be demagnetized and the magnet 48 can again be magnetized so that it will attract the particles to the conception-preventing location.

Of course, when it is desired to restore the implant to the condition shown in FIG. 1 where conception will be prevented, then this same magnet stronger than the magnet 48 or the magnet 50 is again moved in such a way as to attract the particles 42 away from the magnet 50 and into the field of the magnet 48 which now holds the particles again in the position shown in FIG. 1, so that the conception-preventing condition is again restored.

It is thus apparent that with the implant of the invention it is indeed possible to prevent sperm from being expelled with the ejaculate in numbers sufficient for providing conception while at the same time there is no interruption in the flow of the fluid which normally carries the sperm so that pressures resulting from blockage of this fluid are reliably avoided and at the same time hormones and enzymes carried by the fluid continue to be delivered to the body of the individual even though conception is reliably avoided.

Instead of utilizing a pair of barrier means 44 and 46 as described above, it is also possible to use labyrinth types of barrier means. For example a series of coaxial tubes may be arranged one within the other supported in any suitable way as by radially extending pins positioned between and connected with the tubes, and the inner end of the outer tube may have the construction of a channel of U-shaped cross section defining a circular groove which receives in its interior the inner end of the next tube, the outer end of which is closed so that the fluid must flow between the pair of outer tubes and have its direction reversed at the circular channel at the inner end of the outer tube, the third tube being spaced from and surrounded by the second tube and extending from this channel at the inner end of the first tube so that in this way it is possible to provide a zig-zag path for the fluid. Of course the third tube from the outside would be received in a circular groove formed by a flange of U-shaped cross section at the front end of the next inner tube, so that the fluid can be returned to the desired direction of flow toward the outlet. With such a labyrinth type of construction it is also possible to retain the particles while permitting the fluid which normally carries the sperm to flow through the device. For safety purposes small magnets can be positioned at the outer ends of the tubular members 16 and 24 so that if one or more particles should happen to be carried along with the fluid through the labyrinth passage such particles will be retained by such small magnets at the ends of the tubular members and thus prevent it from flowing beyond the device.

In connection with the above description and the claims which follow, reference has been made to the particles 42. While the term "particles" is of course intended to cover extremely small grains of solid material which may have the consistency of a powder, for example, it is also intended for the term particles to cover extremely small members in the form of fine hairs or filaments which will also function in the desired manner as the particles which can be magnetically attracted to form a body in the density of which will reliably retain sperm while permitting the fluid which carries the sperm to continue to flow without the sperm being carried thereby.

What is claimed is:

1. In an implant for reversibly preventing conception, a pair of elongated open-ended tubular means spaced from each other and respectively having inner ends directed toward and outer ends directed away from each other, an intermediate housing means fluid-tightly connected with said pair of tubular means at the regions of said inner ends thereof for defining between said pair of tubular means a space with which both of said tubular means communicate and through which fluid can flow between said pair of tubular means, said housing means having in its interior a particulate means made up of a plurality of fine particles of a material which responds to magnetic forces, said housing means accommodating said particulate means in said housing means for movement between a conception-preventing position in a path of fluid flow between said pair of tubular means and a conception-enabling position out of the path of flow between said pair of tubular means through the interior of said housing means, each of said tubular means carrying at its inner end region a barrier means for permitting fluid to flow through said inner end region of each tubular means while preventing the particles from flowing in any appreciable numbers therethrough, and a permanent magnet means located adjacent said housing means for attracting said particles to said conception-preventing position with a magnetic force urging said particles against each other sufficiently to form from said particles a body having a density sufficiently great to prevent sperm from flowing through said body in numbers sufficient for conception while still permitting fluid in which sperm are normally suspended to flow past the particles, whereby a fluid which normally carries sperm will flow through both of the tubular means while sperm will be retained by said particles when they are in said conception-preventing position, while when the particles are in said conception-enabling position, free flow of fluid with sperm therein is provided when conception is desired.

2. The combination of claim 1 and wherein said permanent magnet means is situated at said housing means around the inner end region of that one of said tubular means which is located downstream with respect to the flow of fluid from the other of said tubular means toward said one tubular means.

3. The combination of claim 2 and wherein said other tubular means which is the upstream tubular means extends at its inner end region into the interior of said housing means through a substantial distance, and said housing means surrounding the part of said upstream tubular means which is situated in the interior of said housing means while being spaced therefrom to an extent sufficient for accommodating said particles when conception is desired.

4. The combination of claim 1 and wherein each of said tubular means includes an inner tubular member and an outer tissue-ingrowth means surrounding and engaging said inner tubular member.

5. The combination of claim 4 and wherein each of said inner tubular members extends outwardly beyond said tissue ingrowth means through a substantial distance and is flexible.

6. The combination of claim 4 and wherein each of said tissue ingrowth means carries at an outer end region thereof beyond which said inner tubular member extends a plurality of barbs for engaging tissue at the exterior of a vas deferens.

7. The combination of claim 6 and wherein the tissue ingrowth means is a wire winding and said barbs form part of a structure which is swaged to said tissue ingrowth means to be joined therewith.

8. The combination of claim 4 and wherein the tissue ingrowth means of each tubular means extends inwardly beyond the tubular member thereof and defines the inner end region of each tubular means, each tissue ingrowth means where it extends inwardly beyond the tubular member of each tubular means surrounding and carrying said barrier means.

9. The combination of claim 8 and wherein each barrier means has the form of a block of filamentary material which has been compressed to an extent sufficient to provide in the interior of the block spaces large enough to permit fluid to flow but too small to receive said particles.

10. The combination of claim 9 and wherein the filamentary material is gold.

11. The combination of claim 4 and wherein the tissue ingrowth means of each tubular means includes a wire winding.

12. The combination of claim 11 and wherein the wire winding is made of gold.

13. The combination of claim 1 and wherein said housing means projects radially beyond said permanent magnet.

14. The combination of claim 1 and wherein the particles are made of a material which cannot become permanently magnetized so that they can be situated in said conception-enabling position by a magnet stronger than said permanent magnet.

15. The combination of claim 1 and wherein a second permanent magnet means is situated at the exterior of said housing surrounding the other of said tubular means at said inner end region thereof for magnetically holding said particles in said conception-enabling position.

* * * * *